United States Patent [19]

Köppe et al.

[11] 4,039,685
[45] Aug. 2, 1977

[54] 1-PHENOXY-2-HYDROXY-3-TERT.-BUTYLAMINO PROPANE ANTIARRHYTHMIC COMPOUNDS

[75] Inventors: Herbert Köppe, Ingelheim am Rhein; Albrecht Engelhardt, Mainz; Karl Zeile, Ingelheim am Rhein, all of Germany

[73] Assignee: Boehringer Ingelheim GmbH, Ingelheim am Rhein, Germany

[21] Appl. No.: 571,790

[22] Filed: Apr. 25, 1975

Related U.S. Application Data

[63] Continuation-in-part of Ser. No. 53,015, July 7, 1970, abandoned, which is a continuation-in-part of Ser. No. 700,376, Jan. 25, 1968, Pat. No. 3,541,130.

[30] Foreign Application Priority Data

| Feb. 6, 1967 | Germany | 91070 |
| June 15, 1967 | Germany | 93025 |
| June 15, 1967 | Germany | 27645/67 |

[51] Int. Cl.² ............... A61K 31/135; C07C 93/06
[52] U.S. Cl. ............................ 424/330; 260/570.7
[58] Field of Search .................. 424/330; 260/570.7

[56] References Cited

U.S. PATENT DOCUMENTS

| 3,379,761 | 4/1968 | Wilhelm | 260/570.7 |
| 3,483,221 | 12/1969 | Wilhelm | 260/326.14 |
| 3,501,769 | 3/1970 | Crowther et al. | 260/57.7 X |
| 3,542,874 | 11/1970 | Keizer et al. | 260/570.7 |
| 3,872,147 | 3/1975 | Köppe et al. | 260/570.7 X |

Primary Examiner—Leonard Schenkman
Attorney, Agent, or Firm—Hammond & Littell

[57] ABSTRACT

A compound selected from the group consisting of racemates of 1-phenoxy-2-hydroxy-3-tert.-butylamino propanes of the formula

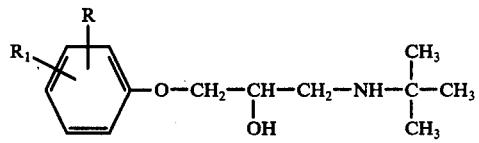

Ia wherein R is selected from the group consisting of alkynyloxy of 2 to 4 carbon atoms, and $R_1$ is selected from the group consisting of hydrogen, halogen and alkoxy of 1 to 4 carbon atoms, their optically active isomers and their non-toxic, pharmaceutically acceptable acid addition salts of said racemates and said optically active isomers which compounds possess bradycardia activity and isoproterenol antagonistic activity and also antiarrhythmic activity.

6 Claims, No Drawings

1-PHENOXY-2-HYDROXY-3-TERT.-BUTYLAMINO PROPANE ANTIARRHYTHMIC COMPOUNDS

PRIOR APPLICATION

This application is a continuation-in-part of our co-pending, commonly assigned U.S. patent application Ser. No. 53,015 filed July 7, 1970, now abandoned, which in turn is a continuation-in-part application of our copending, commonly assigned U.S. patent application Ser. No. 700,376, filed Jan. 25, 1968, now U.S. Pat. No. 3,541,130.

OBJECTS OF THE INVENTION

It is an object of the invention to provide novel 1-(2-alkynyloxy-phenoxy)-2-hydroxy-3-tert.-butylamino propanes of formula Ia and their non-toxic, pharmaceutically acceptable acid addition salts.

It is another object of the invention to provide novel therapeutic compositions having antiarrhythmic activity and to a novel method of inducing antiarrhythmic activity in warm-blooded animals.

These and other objects and advantages of the invention will become obvious from the following detailed description.

THE INVENTION

The novel compounds of the invention are compounds selected from the group consisting of racemates of 1-phenoxy-2-hydroxy-3-tert.-butylamino propanes of the formula

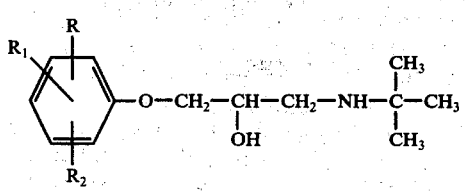

(I)

wherein R is selected from the group consisting of alkynyloxy of 2 to 4 carbon atoms, —(CH$_2$)$_{x+1}$—OH and —NH$_2$x is an integer from 0 to 3, R$_1$ is selected from the group consisting of hydrogen, halogen such as chlorine, bromine, iodine or fluorine and alkoxy of 1 to 4 carbon atoms, their optically active isomers and their non-toxic, pharmaceutically acceptable acid addition salts of said racemates and said optically active isomers.

Examples of non-toxic, pharmacologically acceptable acids suitable for addition salts are inorganic acids such as hydrochloric acid, hydrobromic acid, sulfuric acid, phosphoric acid and organic acids such as methane sulfonic acid, acetic acid, lactic acid, tartaric acid, ascorbic acid, 8-chlorotheophylline and the like.

The compounds according to the present invention may be prepared by a number of different methods involving known chemical reaction principles; however, among these, the following methods have been found to be most convenient and efficient:

Method A

By reacting an epoxide of the formula (II)

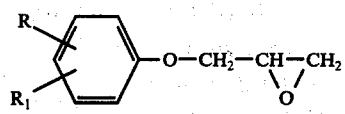

where R and R$_1$ have the same meanings as in formula I, with tert.-butylamine in the presence of an inert organic solvent, such as ethanol.

Method B

By reacting a 1-substituted phenoxy-2-hydroxy-3-halo propane of the formula (III)

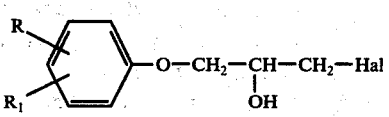

wherein R and R$_1$ have the same meanings as in formula I and Hal is halogen, with tert-butylamine in the presence of an inert organic solvent, such as ethanol.

The starting compounds of the formulas II and III for the above methods are known compounds or may readily be prepared by known methods. For example, the substituted 1-phenoxy-2,3-epoxy propanes of formula II may be prepared by reacting a corresponding substituted phenolate of the formula

wherein M is a monovalent cation, preferably an alkali metal under alkaline conditions with a 1-halo-2,3-epoxy propane such as epichlorohydrin. Most of the corresponding phenols are known in the prior art and they are easily obtainable by conventional methods. Cyanophenols, particularly those with alkoxy groups, may be prepared by splitting off water from the correspondingly substituted phenolic benzaldoximes which are prepared from known phenolic benzaldehydes. Halocyanophenols are obtained by reacting the cyanophenol with a hydrogen halide in the presence of H$_2$O$_2$. The aminomethylphenols are prepared by reduction of the corresponding cyanomethylphenol. The amino substituted phenols are prepared by reacting the corresponding nitrophenols with epichlorohydrin to form the corresponding 2,3-epoxy compound which is reacted with tert.-butylamine and then the nitro group is reduced to the amino group. The hydroxyalkylphenols may be prepared by reduction of the appropriate phenolic benzaldehyde which is then reacted with epichlorohydrin and then with tert.-butylamine. The propargyl oxyphenols can be prepared by reacting propargyl bromide with the appropriate diphenol such as pyrocatechol by heating without any di-substitution which requires more severe reaction conditions. Other processes are described in Belgian Pat. No. 641,133.

The free bases of formula I obtained by any of the above methods, A through G, may be subsequently transformed into non-toxic, pharmacologically acceptable acid addition salts by conventional methods, that is, by acidifying a solution of the free base with the desired acid and recovering the acid addition salt by evaporation of the solvent or by precipitation, for instance.

The compounds of the general formula I possess on the —CHOH— grouping an asymmetric C-atom, and consequently, occur in the form of racemates as well as in the form of optically active antipodes. The optically active compounds can be obtained in that one proceeds either from optically active starting compounds or that the racemates obtained are split into their optical antipodes in the usual manner, for example, by means of dibenzoyl-D-tartaric acid, D-3-bromocamphor-8-sulfonic acid or di-p-tolyl d-tartaric acid.

The compounds according to the present invention, that is those embraced by formula I, and their non-toxic, pharmacologically acceptable acid addition salts, have useful pharmacodynamic properties. More particularly, they produce bradycardia and at the same time act as N-isopropylnoradrenaline (Isoproterenol) antagonists as shown in dogs and guinea pigs. Thus, the tachycardiac effects caused by the administration of N-isopropyl-noradrenaline are suppressed or eliminated by prior administration of one of the compounds of the present invention, and cardiac arrhythmia are equalized by them. In other words, the compounds according to the present invention block the sympathetic nervous system of the heart. Consequently, the areas of indication for the compounds of the present invention are hypertension, angina pectoris, cardiac arrhythmia, digitalis intoxication and pheochromocytoma disorders. They may also be used in conjunction with coronary dilator or sympathicomimetic agents. The compounds of formula I*a* have been formed to have a particularly valuable antiarrhythmic activity.

The compositions of the invention having antiarrhythmic activity are comprised of a small but effective amount of at least one compound selected from the group consisting of racemates of 1-(2-alkynyloxyphenoxy)-2-hydroxy-3-tert.-butylamino propanes of formula I*a*, their optically active isomers and their non-toxic, pharmaceutically acceptable acid addition salts of said racemates and said optically active isomers and a major amount of a pharmaceutical carrier. The compositions may be in the form of injectable solutions or suspensions, tablets, dragees, sustained release tablets, etc. The usual useful dose is 1 to 300 mg, preferably 1 to 150 mg, for oral administration and 1 to 20 mg for parental administration.

The novel method of the invention of inducing antiarrhythmic activity in warm-blooded animals comprises administering to warm-blooded animals a safe and antiarrhythmically effective amount of at least one of the novel compounds of formula I*a*. The said compounds may be administered orally, parentally or rectally. The usual doseage is to mg/kg, depending upon the method of administration.

In the following examples there are described several preferred embodiments to illustrate the invention. However, it should be understood that the invention is not intended to be limited to the specific embodiments.

EXAMPLE 1

Preparation of 1-(2-aminomethyl-4-chlorophenoxy)-2-hydroxy-3-tert.-butylamino propane.2HCl

STEP A:

1-(2-cyano-4-chlorophenoxy-2-hydroxy-3-tert.-butylamino propane . HCl 5.7 gm (0.02 mol) of 1-(2-cyanophenoxy)-2-hydroxy-3-tert.-butylamino propane (prepared analogous to Example II) were dissolved in 32 ml of concentrated HCl and while stirring at 45° C 2.27 gm of 35% hydrogen peroxide were added drowise so that the temperature did not exceed 65° C. Thereafter, the temperature was maintained at 60° C for 30 minutes and the mixture was concentrated in vacuo at the end of which a solid residue remained. The raw hydrochloride was recrystallized from ethanol under an addition of ether to obtain 3 gm of 1-(2-cyano-4-chloro-phenoxy)-2-hydroxy-3-tert.-butylamino propane hydrochloric having a melting point of 180°-182° C.

STEP B:

1-(2-aminomethyl-4-chlorophenoxy)-2-hydroxy-3-tert.-butylamino propane . 2 HCl 6.3 gm (0.02 mol) of 1-(2-cyano-4-chlorphenoxy)-2-hydroxy-3-tert.-butylamino propane hydrochloride were dissolved in 100 ml of methanol containing 10 ml of $NH_3$ and the mixture was hydrogenated under normal pressure at 20° C over Raney-nickel. After separation of the catalyst, the solvent was distilled off in vacuo, and the residue was admixed with ether and water. After an addition of a small amount of NaOH, the aqueous phase was separated and the organic phase was washed with water and dried over $MgSO_4$. After distilling off the ether, a solid residue remained which was recrystallized from ethyl acetate with an addition of petroleum ether to obtain 1-(2-aminomethyl-4-chloro-phenoxy)-2-hydroxy-3-tert.-butylamino propane. The base was dissolved in ethanol and ethereal HCl was added thereto. The precipitated crystals of the hydrochloride of the base were isolated to obtain 3.1 gm of the hydrochloride having a melting point of 118°-120° C.

EXAMPLE 2

Preparation of 1-(2-methoxy-4-aminomethylphenoxy)-2-hydroxy-3-tert.-butylamino-propane. 2 HCl

STEP A:

1-(2-methoxy-4-cyanophenoxy)-2-hydroxy-3-tert.-butylamino propane. HCl 9.9 gm (0.048 mol) of 1-(2-methoxy-4-cyanophenoxy)-2,3-epoxy propane in 100 ml of ethanol were heated with 14.6 gm (0.02 mol; 21 ml) of tert.-butylamine for 3 hours over a water bath. After distillation of the solution in vacuo, the residue was digested with dilute HCl and the solution was separated from the insoluble matter. The aqueous phase was made alkaline with NaOH and the precipitated base was extracted with ether, washed with water, and the organic phase was dried over $MgSO_4$. After distilling off the ether, the oily residue was dissolved in ethanol, admixed with ethereal HCl, and the precipitating crystals of 1-(2-methoxy-4-cyanophenoxy)-2-hydroxy-3-tert.-butylamino propane hydrochloride were vacuum filtered and recrystallized from ethanol with an addition of ether to obtain 7.1 gm of the product having a melting point of 210°-213° C.

STEP B

Using the procedure of Example 1, 1-(2-methoxy-4-cyanophenoxy)-2-hydroxy-3-tert.-butylamino propane hydrochloride was hydrogenated to form 1-(2-methoxy-4-aminomethylphenoxy)-2-hydroxy-3-tert.-butylamino propane dihydrochloride having a melting point of 235°-238° C.

EXAMPLE 3

Preparation of
1-(2-aminomethylphenoxy)-2-hydroxy-3-tert.-butylamino propane . HCl

STEP A:

1-2-(2-cyanophenoxy)-2-hydroxy-3-tert.-butylamino propane . HCl 15 gm (0.085 mol) of 1-2-(2-cyanophenoxy)-2,3-epoxy propane were dissolved in 100 ml of ethanol and 18.6 gm (0.255 mol) of tert.-butylamine were added thereto. After standing for 1 hour at room temperature, the solution was heated at 60°-70° C for 2 hours after which the volatile constituents were distilled off in vacuo. The residue was digested with dilute HCl, and the insoluble constituents were vacuum filtered off. Then the filtrate was made alkaline with NaOH and the precipitating base was taken up in ether. After the ether solution had been dried over MgSO$_4$, the ether was distilled off and the residue was dissolved in ethereal HCl, the hydrochloride was precipitated therefrom in crystalline form which after recrystallization from ethanol with an addition of ether gave 9.8 gm of 1-(2-cyanophenoxy)-2-hydroxy-3-tert.-butylamino propane hydrochloride having a melting point of 163°-165° C.

STEP B

Using the procedure of Example 1, 1-(2-cyanophenoxy)-2-hydroxy-3-tert.-butylamino propane hydrochloride was hydrogenated to obtain 1-(2-aminomethylphenoxy)-2-hydroxy-3-tert.-butylamino propane dihydrochloride having a melting point of 220°-222° C.

EXAMPLE 4

Preparation of
1-(2-methoxy-5-aminomethylphenoxy)-2-hydroxy-3-tert.-butylamino propane .2 HCl Using the procedure of Step A of Example 2, tert.-butylamine and 1-(2-methoxy-5-cyanophenoxy)-2,3-epoxy propane were reacted to form 1-(2-methoxy-5-cyanophenoxy)-2-hydroxy-3-tert.-butylamino propane hydrochloride melting at 149°-152° C.

Using the procedure of Step B of Example 1, the latter product was hydrogenated to obtain 1-(2-methoxy-5-aminomethylphenoxy)-2-hydroxy-3-tert.-butylamino propane dihydrochloride.

EXAMPLE 5

Preparation of
1-(4-aminomethylphenoxy)-2-hydroxy-3-tert.-butylamino propane . 2 HCl

STEP A:

1-(4-cyanophenoxy)-2-hydroxy-3-tert.-butylamino propane . 2 HCl 5.7 gm (0.02 mol) of 3-tert.-butyl-5-(4-cyanophenoxymethyl)-oxazolidinone-(2) were dissolved in 50 ml of ethanol. After addition of a solution of 10 gm of potassium hydroxide in 15 ml of water, the solution was refluxed for 2 hours and then the ethanol was distilled off in vacuo, and the residue was extracted with ether. The ethereal phase was separated, dried over MgSO$_4$ and the MgSO$_4$ was filtered off. After concentration of the ether solution, the solid raw base was recrystallized from ethyl acetate to obtain a product having a melting point of 100°-105° C. After dissolving the crystalline base in ethanol, ethereal hydrochloric acid was added and the solid was isolated and again recrystallized from ethanol/ether to obtain 1.9 gm of 1-(4-cyanophenoxy)-2-hydroxy-3-tert.-butylamino propane hydrochloride having a melting point of 187°-189° C.

STEP B

Using the procedure of Example 1, the latter product was hydrogenated to obtain 1-(4-aminomethylphenoxy)-2-hydroxy-3-tert.-butylamino propane dihydrochloride.

EXAMPLE 6

Preparation of
1-(3-aminomethylphenoxy)-2-hydroxy-3-tert.-butylamino propane . HCl

STEP A:

1-(3-cyanophenoxy)-2-hydroxy-3-tert.-butylamino propane oxalate 9.6 gm (0.05 mol of 1-(3-cyanophenoxy)-2-hydroxy-3-amino propane were dissolved in 40 ml of dimethylformamide and 100 ml of tetrahydrofuran and 4.2 gm (0.05 mol) of pulverized sodium bicarbonate were added thereto. Then, 6.9 gm (0.05 mol) of tert.-butylbromide were added and the mixture was refluxed for 24 hours. After the mixutre had been cooled, the inorganic solid was filtered off and the solvent mixture was distilled off in vacuo. The residue was dissolved by heating in ethyl acetate and the insoluble inorganic portions were vacuum filtered off and the filtrate was admixed with petroleum ether. The base precipitated in solid form and was isolated and recrystallized from ethyl acetate with an addition of petroleum ether to obtain 1-(3-cyanophenoxy)-2-hydroxy-3-tert.-butylamino propane having a melting point of 108°-110° C.

STEP B

Using the procedure of Example 1, the latter product was hydrogenated to obtain 1-(3-aminomethylphenoxy)-2-hydroxy-3-tert.-butylamino propane dihydrochloride.

EXAMPLE 7

1-(2nitro-4-chlorophenoxy)-2-hydroxy-3-tert.-butylamino propane was hydrogenated in the presence of Raney-nickel in methanol to obtain 1-(2-amino-4-chloro-phenoxy)-2-hydroxy-3-tert.-butylamino propane dihydrochloride having a melting point of 260°-262° C.

Using the same procedure, the following compounds could be prepared by hydrogenation of the corresponding nitro compound: 1-(2-amino-4-fluorophenoxy)-2-hydro-3tert.-butylamino propane dihydrochloride; 1-(2-amino-5-bromophenoxy)-2-hydroxy-3-tert.-butylamino propane dihydrochloride; and 1-(2-amino-4,6-dichlorophenoxy)-2-hydroxy-3-tert.-butylamino propane dihydrochloride.

EXAMPLE 8

Preparation of
1-(2-,4-dichloro-3-aminophenoxy)-2-hydroxy-3-tert.-butylamino propane . 2HCl 8.05 gm of 1-(3-nitrophenoxy)-2-hydroxy-3-tert.-butylamino propane were dissolved in 100 cc of concentrated hydrochloric acid with stirring and the resulting solution was heated to 45° C. Then 11.3 gm (0.1 mol) of 30% hydrogen peroxide solution were added dropwise while holding the temperature between 50° C and 60° C with stirring. After 30 minutes, an oil separated and excess hydrochloric acid was distilled off in vacuo. The residue was taken up in water and the mixture was made alkaline with sodium hydroxide. The resulting free base precipitated as an oil and was dissolved in ethylacetate. The said solution was washed with water, dried and evaporated to dryness to obtain 9.2 gm (0.0273 mol) of 1-(2,4-dichloro-3-nitrophenoxy)-2-hydroxy-3-tert.-butylamino propane.

The 9.2 gm of the said base were dissolved in 150 cc of methanol and the said base was hydrogenated in the presence of a Raney nickel catalyst at room temperature and normal pressure until the theoretical amount of hydrogen (1840 cc) was adsorbed (2½ hours). The catalyst was then removed by suction filtration and the solvent was distilled off in vacuo. The residue was dissolved in ethanol and the resulting solution was acidified with etherified hydrochloric acid and extracted with ether. After standing in the cold, the dihydrochloride of 1-(2,4-dichloro-3-aminophenoxy)-2-hydroxy-3-tert.-butylamino propane crystallized out. After crystallization twice from acetonitrile, there was obtained 2.5 gm of the dihydrochloride melting at 166°–169° C.

EXAMPLE 9

Preparation of
1-(2-propargyloxyphenoxy)-2-hydroxy-3-tert.-butylamino propane oxalate 7.15 gm (0.035 mol) of 1-(2-propargyloxyphenoxy)-2,3-epoxy propane were dissolved in 70 ml of ethanol and after 11 gm (0.15 mol) of tert.-butylamine were added thereto, the mixture was refluxed for 2 hours. After the mixture was cooled, the solvent was distilled off in vacuo and the oily residue was digested with dilute HCl. The aqueous phase was extracted with ether and the acid, aqueous solution was then made alkaline with NaOH. The base precipitating in oily form was taken up in ether and the organic phase was washed with water and dried over MgSO$_4$. After the ether had been distilled off, the residue was dissolved in absolute ether, and a solution of 2 gm of oxalic acid in 10 ml of acetone was added. The precipitating oxalate was recrystallized from ethanol with an addition of ether to obtain 4.6 gm of 1-(2-propargyloxyphenoxy)-2-hydroxy-3-tert.-butylamino propane oxalate having a melting point of 132°–134° C.

EXAMPLE 10

Using the procedure of Example 9, tert.-butylamine and 1-(2-hydroxymethylphenoxy)-2,3-epoxy propane were reacted to form 1-(2-hydroxymethylphenoxy)-2-hydroxy-3-tert.-butylamino propane oxalate having a melting point of 180°–183° C.

EXAMPLE 11

Using the procedure of Example 9, 20 gm of 1-(3-hydroxymethylphenoxy)-2,3-epoxy propane and 18.5 gm of tert.-butylamine were reacted to obtain 1-(3-hydroxy-methylphenoxy)-2-hydroxy-3-tert.-butylamino propane having a melting point of 82°–84° C.

PHARMACEUTICAL EXAMPLES

EXAMPLE A

| TABLETS | |
|---|---|
| 1. 1-(2-propargyloxyphenoxy)-2-hydroxy-3-tert.-butylamino propane . HCl | 35.0 parts |
| 2.6-bis-(diethylamino)-4,8-dipiperidino-pyrinido-pyrinidine | 75.0 parts |
| lactose | 164.0 parts |
| corn starch | 194.0 parts |
| colloidal silicic acid | 14.0 parts |
| polyvinylpyrrolidone | 6.0 parts |
| magnesium stearate | 2.0 parts |
| soluble starch | 10.0 parts |
| | 500.0 parts |

The individual components are intensively admixed and the mixture is granulated in the usual manner. The granulate is compressed into 1000 tablets of 500 mg, 445 mg or 515 mg.

EXAMPLE B

| GELATIN CAPSULES | |
|---|---|
| The content of the capsules is composed as follows: | |
| 1. 1-(2-propargyloxyphenoxy)-2-hydroxy-3-tert.-butylamino propane . HCl | 25.0 mg |
| Corn starch | 175.0 mg |
| | 200.0 mg |

The ingredients are intensively admixed and 200 mg portions of the mixtures are filled into gelatin capsules of suitable size. Each capsule contains 25 mg of the optically active substance.

EXAMPLE C

| INJECTABLE SOLUTION | |
|---|---|
| 1-(2-propargyloxyphenoxy)-2-hydroxy-3-tert.-butylamino propane hydrochloride | 2.5 parts |
| Sodium salt of EDTA (ethylenediaminetetraacetic acid) | 0.2 parts |
| distilled water ad. | 100.0 parts |

Preparation

The active substance and the EDTA-salt were dissolved in sufficient water and distilled water to the desired volume was added. The solution was filtered free of suspended particles and filled into 1-cm-ampules under aseptic conditions. Then, the ampoules were sterilized and sealed so that each of these ampoules contained 25 mg of active substance.

EXAMPLE D

| SUSTAINED RELEASE TABLETS | |
|---|---|
| 1. Racemic 1-(2-propargyloxyphenoxy)-2-hydroxy-3-tert.-butylamino propane . HCl | 25.0 gm |
| carboxymethylcellulose (CMC) | 295.0 gm |
| stearic acid | 20.0 gm |
| cellulose acetate phthalate (CAP) | 40.0 gm |
| | 380.0 gm |

The active substance, the carboxymethylcellulose and the stearic acid are intensively admixed and the mixture is granulated in the usual manner, a solution of the cellulose acetate phthalate in 200 ml of a mixture of ethanol and ethylacetate is used for this purpose. The granulate is then compressed into 380 mg kernels, which are in the usual manner coated with a sugar containing 5% solution of polyvinylpyrrolidone in water. Each tablet contains 25 mg of active ingredients.

Various modifications of the compositions and method of the invention may be made without departing from the spirit or scope thereof, and it is to be understood that the invention is to be limited only as defined in the appended claims.

We claim:

1. A compound selected from the group consisting of racemates of 1-phenoxy-2-hydroxy-3-tert.-butylamino propanes of the formula

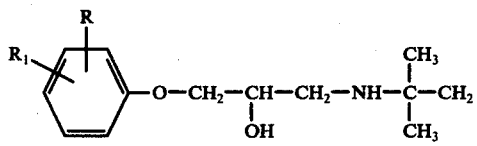

where R is alkynyloxy of 2 to 4 carbon atoms, $R_1$ is selected from the group consisting of hydrogen, halogen and alkoxy of 1 to 4 carbon atoms, their optically active isomers and their non-toxic, pharmaceutically acceptable acid addition salts of said racemates and said optically active isomers.

2. A compound of claim 1 wherein $R_1$ is hydrogen.

3. A compound of claim 1 which is selected from the group consisting of 1-(2-propargyloxyphenoxy)-2-hydroxy-3-tert.-butylamino propane and its non-toxic, pharmaceutically acceptable acid addition salts.

4. A therapeutic composition having antiarrhythmic acitivity comprising a safe and effective amount of a compound of claim 1 and a major amount of a pharmaceutical carrier.

5. A method of inducing antiarrhythmic acitivity in warm-blooded animals comprising administering to warm-blooded animals an antiarrhythmically effective amount of a compound of claim 1.

6. The method of claim 5 wherein the compound is selected from the group consisting of 1-(2-propargyloxyphenoxy)-2-hydroxy-3-tert.-butylamino propane and its non-toxic, pharmaceutically acceptable acid addition salts.

* * * * *